United States Patent
Brockunier et al.

(10) Patent No.: US 7,253,172 B2
(45) Date of Patent: Aug. 7, 2007

(54) DIPEPTIDYL PEPTIDASE INHIBITORS FOR THE TREATMENT OF DIABETES

(75) Inventors: Linda Brockunier, Orange, NJ (US); Emma Parmee, Scotch Plains, NJ (US); Ann E. Weber, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 297 days.

(21) Appl. No.: 10/481,359

(22) PCT Filed: Jun. 19, 2002

(86) PCT No.: PCT/US02/19441

§ 371 (c)(1),
(2), (4) Date: Dec. 18, 2003

(87) PCT Pub. No.: WO03/000181

PCT Pub. Date: Jan. 3, 2003

(65) Prior Publication Data

US 2004/0236102 A1 Nov. 25, 2004

Related U.S. Application Data

(60) Provisional application No. 60/299,505, filed on Jun. 20, 2001.

(51) Int. Cl.
*A61K 31/495* (2006.01)
*C07D 401/06* (2006.01)
*C07D 403/06* (2006.01)
*C07D 413/06* (2006.01)
*C07D 405/06* (2006.01)

(52) U.S. Cl. .......................... 514/252.13; 514/252.14; 514/252.17; 514/254.11; 514/254.04; 514/253.01; 514/254.09; 544/373; 544/360; 544/295; 544/374; 544/377; 544/368

(58) Field of Classification Search ................ 544/373, 544/360, 295, 374, 368, 377; 514/254.09, 514/253.01, 252.14, 252.13, 254.04, 252.17, 514/254.11
See application file for complete search history.

(56) References Cited

U.S. PATENT DOCUMENTS

| 4,386,090 A | 5/1983 | Moinet et al. |
| 5,939,560 A | 8/1999 | Jenkins et al. |

FOREIGN PATENT DOCUMENTS

| WO | WO 9719908 | * | 6/1997 |
| WO | WO 97/40832 A1 | | 11/1997 |
| WO | WO 98/19998 A2 | | 5/1998 |
| WO | WO 98/19998 A3 | | 5/1998 |
| WO | WO 9856771 | * | 12/1998 |
| WO | WO 00/34241 A1 | | 6/2000 |
| WO | WO 01/34594 A1 | | 5/2001 |
| WO | WO 01/96295 A2 | | 12/2001 |
| WO | WO 01/96295 A3 | | 12/2001 |
| WO | WO 02/02560 A2 | | 1/2002 |
| WO | WO 02/02560 A3 | | 1/2002 |
| WO | WO 02/076450 A1 | | 10/2002 |
| WO | WO 03/000180 A2 | | 1/2003 |
| WO | WO 03/000180 A3 | | 1/2003 |
| WO | WO 03/000181 A2 | | 1/2003 |
| WO | WO 03/000181 A3 | | 1/2003 |
| WO | WO 03/004498 A1 | | 1/2003 |
| WO | WO 03/082817 A2 | | 10/2003 |

OTHER PUBLICATIONS

Deacon et al. Expert Opin. Investig. Drugs (2004) 13(9): 1091-1102.*
Expert Opinion onTherapeutic Patents, "Novel N-substituted-2-cyanopyrrolidines as potent inhibitors of dipeptidyl peptidase IV in the treatment of non-insulin-dependent diabetes mellitus", vol. 10 (#12) p. 1937-1942 (2000).
Expert Opinion on Investig. Drugs, "Gut peptides in the treatment of diabetes mellitus", (2004) 13 (3) 177-188.
Expert Opinion on Investig. Drugs, "Therapeutic potential of dipeptidyl peptidase IV inhibitors for the treatment of type 2 diabetes", (2003) 12: 87-100.
Expert Opinion on Therapeutic Patents, "Dipeptidyl peptidase IV inhibitors as new therapeutic agents for the treatment of Type 2 diabetes", (2003) 13: 499-510.

* cited by examiner

*Primary Examiner*—Rebecca Anderson
(74) *Attorney, Agent, or Firm*—Philippe L. Durette; Catherine D. Fitch

(57) ABSTRACT

Compounds having Formula I, including pharmaceutically acceptable salts and prodrugs thereof: (I) are inhibitors of the dipeptidyl peptidase-IV enzyme (DP-IV), and are useful in the treatment of DP-IV mediated diseases and conditions, such as non-insulin dependent diabetes mellitus

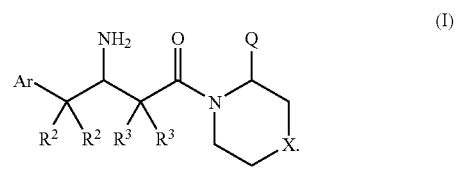

(I)

11 Claims, No Drawings

DIPEPTIDYL PEPTIDASE INHIBITORS FOR THE TREATMENT OF DIABETES

CROSS REFERENCE TO RELATED APPLICATIONS

This application is the National Stage of International Application No. PCT/US02/19441, filed Jun. 19, 2002, which claims the benefit under 35 U.S.C. 119(e) of U.S. Provisional Application No. 60/299,505, filed Jun. 20, 2001.

FIELD OF THE INVENTION

The instant invention is concerned with a novel class of dipeptidyl peptidase inhibitors, including pharmaceutically acceptable salts and prodrugs thereof, which are useful as therapeutic compounds, particularly in the treatment of Type 2 diabetes mellitus, often referred to as non-insulin dependent diabetes (NIDDM), and of conditions that are often associated with this disease, such as obesity and lipid disorders.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV enzyme are also under investigation as drugs that may be useful in the treatment of diabetes, and particularly type 2 diabetes. See for example WO 97/40832 and WO 98/19998. The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors may also have other therapeutic utilities, as discussed elsewhere in this application. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

A new class of DP-IV inhibitors is described herein. They may be effective in the treatment of Type 2 diabetes and other DP-IV modulated diseases. The class of compounds is defined by formula I below, including pharmaceutically acceptable salts and prodrugs.

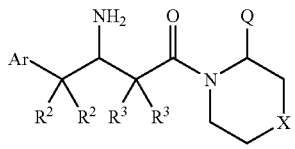

In the compounds having Formula I:
X is selected from $CH_2$, O and $NR^7$;
Ar is selected from the group consisting of:
(1) phenyl,
(2) naphthyl,
(3) thienyl, and
(4) benzothiophenyl, wherein Ar is optionally substituted with 1–5 groups $R^1$;
$R^1$ is selected from the group consisting of:
(1) halogen,
(2) $C_{1-6}$alkyl, which is linear or branched and is optionally substituted with 1–5 halogens,
(3) $OC_{1-6}$alkyl, which is linear or branched and is optionally substituted with 1–5 halogens, and
(4) CN;

Each $R^2$ is independently selected from the group consisting of H, OH, halogen and $C_{1-6}$alkyl, wherein $C_{1-6}$alkyl is linear or branched and is optionally substituted with 1–5 halogens, wherein the two groups $R^2$ can optionally be joined to form a $C_{3-6}$cycloalkyl, which is optionally substituted with 1–3 halogens;

Each $R^3$ is independently selected from the group consisting of H, halogen and $C_{1-6}$alkyl, wherein $C_{1-6}$alkyl is linear or branched and is optionally substituted with 1–5 halogens, wherein the two groups $R^3$ can optionally be joined to form a $C_{3-6}$cycloalkyl, which is optionally substituted with 1–3 halogens;

Q is selected from the group consisting of:
(1) H,
(2) $C_{1-10}$alkyl, which is linear or branched and is optionally substituted with 1–6 substituents independently selected from 0–5 halogens and 0–1 substituent selected from
(a) phenyl,
(b) naphthyl,
(c) a 5 or 6-membered heterocycle which may be saturated or unsaturated comprising 1–4 heteroatoms independently selected from N, S and O,
(d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O,
(e) $CO_2H$,
(f) $CO_2C_{1-6}$alkyl, and
(g) $CONR^4R^4$ wherein said phenyl and naphthyl are optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens, and wherein said $CO_2C_{1-6}$alkyl is linear or branched, and wherein said 5 or 6-membered heterocycle and said 8–10 membered bicyclic ring system are optionally substituted with 1–5 substituents independently selected from $C_{1-6}$alkyl, $OC_{1-6}$alkyl, oxo, hydroxy and halogen, said $C_{1-6}$alkyl and $OC_{1-6}$alkyl being linear or branched and optionally substituted with 1–5 halogens, and wherein said $CO_2C_{1-6}$alkyl is linear or branched;
(3) CN;
(4) Phenyl, which is optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens;
(5) Naphthyl, which is optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens,
(6) a 5 or 6-membered heterocycle which may be saturated or unsaturated comprising 1–4 heteroatoms independently selected from N, S and O, said heterocycle being optionally substituted with 1–5 substituents independently selected from oxo, hydroxy, $C_{1-6}$alkyl, $OC_{1-6}$alkyl and halogen, said $C_{1-6}$alkyl and $OC_{1-6}$alkyl being linear or branched and optionally substituted with 1–5 halogens, and
(7) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O, wherein said bicyclic ring system is optionally substituted with 1–5 substituents independently selected from oxo, hydroxy, $C_{1-6}$alkyl, $OC_{1-6}$alkyl and halogen, said $C_{1-6}$alkyl and $OC_{1-6}$alkyl being linear or branched and optionally substituted with 1–5 halogens;

$R^4$ is selected from
(1) H, and
(2) $R^5$;

$R^5$ is selected from the group consisting of phenyl, $C_{3-6}$cycloalkyl and $C_{1-6}$alkyl, wherein $C_{1-6}$alkyl is linear or branched and is optionally substituted with 1–6 substituents independently selected from 0–5 halogens and 0–1 phenyl, wherein said optional phenyl substituent and said $R^5$ when R5 is phenyl or $C_{3-6}$cycloalkyl are optionally substituted with 1–5 substituents independently selected from halogen, OH, $C_{1-6}$alkyl, and $OC_{1-6}$alkyl, said $C_{1-6}$alkyl and $OC_{1-6}$alkyl being linear or branched and optionally substituted with 1–5 halogens; and $R^7$ is selected from the group consisting of
(1) H,
(2) $C_{1-6}$alkyl which is linear or branched and is optionally substituted with 1–6 substituents independently selected from 0–5 halogens and 0–1 substituents selected from
(a) phenyl,
(b) naphthyl, (c) a 5 or 6-membered heterocyclic ring which may be saturated or unsaturated comprising 1–4 heteroatoms independently selected from N, S and O,
(d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O,
(e) C(=O)NR$^4$R$^4$, wherein said phenyl, naphthyl, and R$^4$ when R$^4$ is phenyl or C$_{3-6}$cycloalkyl are optionally substituted with 1–5 substituents independently selected from halogen, OH, nitro, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, and wherein said 5–6-membered heterocycle and 8–10 membered bicyclic ring system are optionally substituted with 1–5 substituents independently selected from halogen, oxo, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, (3) Phenyl, which is optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens, (4) a 5 or 6-membered heterocycle which may be saturated or unsaturated comprising 1–4 heteroatoms independently selected from N, S and O, wherein said heterocycle is optionally substituted with 1–5 substituents independently selected from halogen, oxo, OH, C$_{1-6}$alkyl and OC$_{1-6}$alkyl, said C$_{1-6}$alkyl and OC$_{1-6}$alkyl being linear or branched and optionally substituted with 1–5 halogens, (5) an 8–10 membered bicyclic ring system which may be saturated or unsaturated which comprises (a) two fused heterocyclic rings, each heterocyclic ring having 1–4 heteroatoms selected from N, S and O, or (b) a 5- or 6-membered heterocycle having 1–3 heteroatoms selected from N, S and O fused to a pheny ring, wherein said bicyclic ring system is optionally substituted with 1–5 substituents independently selected from halogen, oxo, OH, C$_{1-6}$alkyl and OC$_{1-6}$alkyl, said C$_{1-6}$alkyl and OC$_{1-6}$alkyl being linear or branched and optionally substituted with 1–5 halogens, and (6) adamantyl, which is optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens;

(7) naphthyl, which is optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens; and (8) a 5–6 membered cycloalkyl fused to a phenyl ring, wherein said cycloalkyl may be saturated or unsaturated, wherein said cycloalkyl and fused phenyl ring are optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens.

DETAILED DESCRIPTION OF THE INVENTION

The compounds having Formula I have numerous preferred embodiments, which are described below.

In embodiments of Formula I, R$_2$ is H. In other embodiments, R$_3$ is H. In many embodiments, R$^2$ and R$^3$ are both H.

In preferred embodiments, Ar is phenyl, which is optionally substituted as described above.

In other embodiments, R$^4$ is H.

A preferred embodiment comprises compounds having formula I in which Q is selected from the group consisting of phenyl and CH$_2$phenyl, optionally substituted as described above.

Another embodiment comprises compounds having formula I as recited in claim 1, wherein X is NR$^7$, and R$^7$ is CH$^2$, which is substituted with 1 substituent selected from (a) phenyl;
(b) naphthyl;
(c) a 5 or 6-membered heterocyclic ring which may be saturated or unsaturated comprising 1–4 heteroatoms independently selected from N, S and O;
(d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O, and
(e) C(=O)NR$^4$R$^4$, wherein R$^4$ is as previouly defined, and said phenyl, naphthyl, and R$^4$ when R$^4$ is phenyl or C$_{3-6}$cycloalkyl are optionally substituted with 1–5 substituents independently selected from halogen, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, and wherein said 5–6-membered heterocycle and 8–10 membered bicyclic ring system are optionally substituted with 1–5 substituents independently selected from halogen, oxo, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens.

In the compounds described above, the 8–10 membered bicyclic ring system is preferably selected from the group consisting of indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, isoquinoline, tetrahydroisoquinoline, and dihydroisoquinoline, substituted as described above. Indole is a preferred 8–10 membered bicyclic ring system.

Preferably, 5- or 6-membered heterocycles are selected from furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, and tetrazolidine. More preferred heterocycles include imidazole, morpholine, pyrazole, pyridine, tetrazole, thiazole and triazole.

Definitions

"Ac" is acetyl, which is $CH_3C(O)$—.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a mono- or bicyclic saturated carbocyclic ring having from 3 to 10 carbon atoms. The term also can refer to a cycloalkyl ring fused to another ring such as an aromatic ring. Examples of cycloalkyl include cyclopropyl, cyclopentyl, cyclohexyl, cycloheptyl, and the like.

"Aryl" (and "arylene") means a mono- or polycyclic aromatic ring system containing only carbon ring atoms. The term "aryl" also includes an aryl group fused to a cycloalkyl or heterocycle, where aryl refers to the aromatic portion. The preferred aryls are phenyl and naphthyl. The most preferred aryl is phenyl.

"Heterocycle" means a saturated or unsaturated ring (including aromatic rings) containing at least one heteroatom selected from N, S and O (including SO and $SO_2$). Examples of heterocycles include tetrahydrofuran, piperazine, morpholine and sulfolane.

"Heteroaryl" (and heteroarylene) means an aromatic heterocycle that contains at least one ring heteroatom selected from N, O and S (including SO and $SO_2$). Heteroaryls can be fused to other heteroaryls or to other kinds of rings, such as aryls, cycloalkyls or heterocycles that are not aromatic. Examples of monocyclic heteroaryls and heteroaryls fused to other rings (aryl or heteroaryl) include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, dibenzofuran and the like.

"Halogen" includes fluorine, chlorine, bromine and iodine. Chlorine and fluorine are generally preferred.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Optical Isomers-Diastereomers-Geometric Isomers-Tautomers

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of Formula I.

Formula I shows the structure of the class of compounds without preferred stereochemistry. Formula Ia shows the preferred sterochemistry at the carbon atom that is attached to the amine group of the beta amino acid from which these compounds are made.

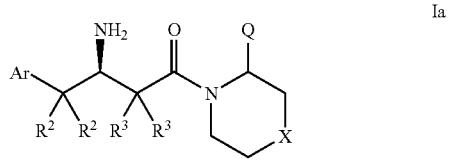

Ia

Formula Ib shows the preferred sterochemistry at the carbon atom that is attached to the amine group of the beta amino acid from which these compounds are made and at the carbon atom attached to substituent Q.

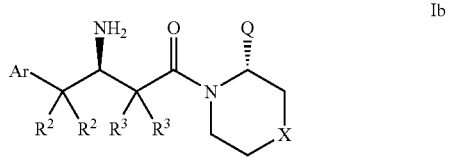

Ib

The various substituent groups in the compounds of Formula Ia and Ib are the same as those described previously for the compounds having Formula I.

If desired, racemic mixtures of compounds of Formula I may be separated so that the individual enantiomers are isolated. The separation can be carried out by methods well known in the art, such as the coupling of a racemic mixture of compounds of Formula I to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds of Formula I can also be separated directly by chromatographic methods utilizing chiral stationary phases, which methods are well known in the art.

Alternatively, any enantiomer of a compound of the general Formula I may be obtained by stereoselective synthesis using optically pure starting materials or reagents of known configuration. Such methods are well known in the art.

Compounds of Formula I may have more than one asymmetric center, as can be seen in FIG. Ib. Such compounds may occur as mixtures of diasteromers, which can be separated into individual diasteromers by standard methods, and the diastereomers can be further separated to individual enantiomers as described above.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

Metabolites of the compounds of this invention that are therapeutically active and that are defined by Formula I or Ia are also within the scope of this invention. Prodrugs are compounds that are converted to therapeutically active compounds as they are being administered to a patient or after they have been administered to a patient. Prodrugs which are subsequently converted to a compound defined by Formula I during or after administration are also within the scope of the invention, as are the active metabolites of the prodrug. A non-limiting example of a prodrug of a compound having Formula I is a compound in which the amine group is functionalized with a group or groups that are removed under physiological conditions after administration to a mammalian patient to yield a compound having Formula I, or a pharmaceutically acceptable salt thereof.

Utilities

DP-IV is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes.

1. Type II Diabetes and Related Disorders

It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP, glucagon). Inactivation of these peptides by DP-IV may also play a role in glucose homeostasis.

The DP-IV inhibitors of this invention therefore may have utility in the treatment of type II diabetes and in the treatment and prevention of the numerous conditions that often accompany Type II diabetes, including metabolic syndrome X, reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore some or all of these may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component.

2. Obesity

There is an expectation that DP-IV inhibitors may be useful for the treatment of obesity. This expectation is based on the observed inhibitory effects on food intake and gastric emptying of GLP-1 and GLP-2. Exogenous administration of GLP-1 in humans significantly decreases food intake and slows gastric emptying (Am. J. Physiol. 277, R910–R916 (1999)). ICV administration of GLP-1 in rats and mice also has profound effects on food intake (Nature Medicine 2, 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (Nature Medicine 6, 802–807 (2000)).

3. Growth Hormone Deficiency

DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3–44] (BBA 1122, 147–153 (1992)); (2) GRF is rapidly degraded in plasma to GRF[3–44]; this is prevented by the DP-IV inhibitor diprotin A; and (3) GRF[344] is found in the plasma of a human GRF transgenic pig (J. Clin. Invest. 83, 1533–1540 (1989)). Thus DP-IV inhibitors may be useful for the same spectrum of indications which have been considered in the case of Growth Hormone secretagogues.

4. Intestinal Injury

The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (Regulatory Peptides 90, 27–32 (2000)). Administration of GLP-2 results in increased small bowel mass in rodents and attenuates intestinal injury in rodent models of colitis and enteritis.

5. Immunosuppression

It has been suggested that DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation.

A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (Transplantation 63, 1495–1500 (1997)). DP-IV inhibitors have been tested in collagen and alkyldiamine-induced arthritis in rats and showed a statistically significant attenuation of hind paw swelling in this model (Int. J. Immunopharmacology 19, 15–24 (1997), Immunopharmacology 40, 21–26 (1998)).

DP-IV is upregulated in a number of autoimmune diseases including rheumatoid arthritis, multiple sclerosis, Graves' disease, and Hashimoto's thyroiditis (Immunology Today 20, 367–375 (1999)).

6. HIV Infection

A number of chemokines which inhibit HIV cell entry are potential substrates for DP-IV (Immunology Today 20, 367–375 (1999)). In the case of SDF-1alpha, cleavage decreases antiviral activity (PNAS 95, 6331–6 (1998)). Thus, stabilization of SDF-1alpha through inhibition of DP-IV would be expected to decrease HIV infectivity.

7. Hematopoiesis

It has been suggested that DP-IV may be involved in hematopoiesis. A DP-IV inhibitor, Val-Boro-Pro, stimulates hematopoiesis in a mouse model of cyclophosphamide-induced neutropenia (WO 99/56753).

8. Neuronal Disorders

A number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6 M^{-1} s^{-1}$ or greater. In an electric shock jump test model of analgesia in rats, a DP-IV inhibitor showed a significant effect that was independent of the presence of exogenous endomorphin-2 (Brain Research 815, 278–286 (1999)).

9. Tumor Invasion and Metastasis

An increase or decrease in expression of several ectopeptidases including DP-IV has been observed during the transformation of normal cells to a malignant phenotype (J. Exp. Med. 190, 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

10. Benign Prostatic Hypertrophy

Increased DP-IV activity was noted in prostate tissue from patients with BPH (Eur. J. Clin. Chem. Clin. Biochem 30, 333–338 (1992)).

11. Sperm Motility/Male Contraception

In seminal fluid, prostatosomes, prostate derived organelles important for sperm motility, possess very high levels of DP-IV activity (Eur. J. Clin. Chem. Clin. Biochem 30, 333–338 (1992)).

12. Gingivitis

DP-IV activity was found in gingival crevicular fluid and in some studies correlated with periodontal disease severity (Arch. Oral Biol. 37, 167–173 (1992)).

13. Osteoporosis

GIP receptors are present in osteoblasts.

It is therefore anticipated that the compounds of Formula I, Ia and Ib may have utility in treating one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (32) gingivitis, (33) hypertension,

(34) osteoporosis, and other conditions that may be treated by inhibition of DP-IV, wherein said treatment comprises the administration to a human or mammalian patient of a therapeutically effective amount of a compound having Formula I, including pharmaceutically acceptable salts and prodrugs.

Combination Therapy

Compounds of Formula I may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PIP-1B) inhibitors;

(c) insulin or insulin mimetics;

(d) sulfonylureas and other insulin secretagogues such as tolbutamide and glipizide, meglitinide, and related materials;

(e) α-glucosidase inhibitors (such as acarbose);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (i) HMG-CoA reductase inhibitors (lovastatin, simvastatin, pravastatin, fluvastatin, atorvastatin, rivastatin, itavastatin, rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as for example ezetimibe and beta-sitosterol, (vii) acyl CoA:cholesterol acyltransferase inhibitors, such as for example avasimibe, and (viii) antioxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide Y5 inhibitors, and β3adrenergic receptor agonists;

(m) an ileal bile acid transporter inhibitor; and (n) agents intended for use in inflammatory conditions such as aspirin, non-steroidal anti-inflammatory drugs, glucocorticoids, azulfidine, and cyclo-oxygenase 2 selective inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and anti-obesity compounds.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt or prodrug thereof as an active ingredient, as well as a pharmaceutically acceptable carrier. Optionally other therapeutic ingredients or other DP-IV inhibitors, or both, may be included in the pharmaceutical compositions as discussed previously. The term "pharmaceutically acceptable salts"

refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants

Inhibition constants were determined as follows. A continuous fluorometric assay was developed with the substrate Gly-Pro-AMC, which is cleaved by DP-IV to release the fluorescent AMC leaving group. The kinetic parameters that describe this reaction are as follows: $K_m=50\ \mu M$; $k_{cat}=75s^{-1}$; $k_{cat}/K_m=1.5\times10^6\ M^{-1}s^{-1}$. A typical reaction contains approximately 50 pM enzyme, 50 μM Gly-Pro-AMC, and buffer (100 mM HEPES, pH 7.5, 0.1 mg/ml BSA) in a total reaction volume of 100 μl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. Unless otherwise indicated, the enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme.

The compounds described herein generally have inhibition constants of less than 10 μM. Preferred compounds have inhibition constants of less than 1 μM. Highly preferred compounds have inhibition constants of less than 300 nM.

To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

Synthetic Schemes

The compounds (I) of the present invention can be prepared from beta amino acid intermediates such as those of formula II and substituted heterocyclic intermediates such as those of formula III, using standard peptide coupling conditions followed by deprotection. The preparation of these intermediates is described in the following schemes.

II

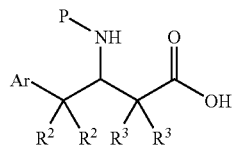

-continued

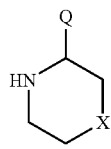
III where Ar, $R^2$, $R^3$, Q, and X are as defined above and P is a suitable nitrogen protecting group such as tert-butoxycarbonyl, benzyloxycarbonyl, or 9-fluorenylmethoxycarbonyl.

Compounds IIa, where $R^3$ is hydrogen, are commercially available, known in the literature or may be conveniently prepared by a variety of methods familiar to those skilled in the art. One common route is illustrated in Scheme 1. Acid 1, which may be commercially available or readily prepared from the corresponding amino acid by protection using, for example, N-(9-fluorenylmethoxycarbonyloxy)succinimide, is treated with isobutylchloroformate and diazomethane using a base such as triethylamine. The resultant diazoketone is then treated with silver benzoate in aqueous dioxane and may be subjected to sonication following the procedure of Sewald et al., *Synthesis*, 837 (1997) in order to provide the beta amino acid IIa. As will be understood by those skilled in the art, for the preparation of enantiomerically pure beta amino acids II, enantiomerically pure alpha amino acids 1 may be used. Alternate routes to these compounds can be found in the following reviews: E. Juaristi, *Enantioselective Synthesis of β-Amino Acids*, Ed., Wiley-VCH, New York: 1997, Juaristi et al., *Aldrichimica Acta*, 27, 3 (1994), Cole et al., *Tetrahedron*, 32, 9517 (1994).

SCHEME 1

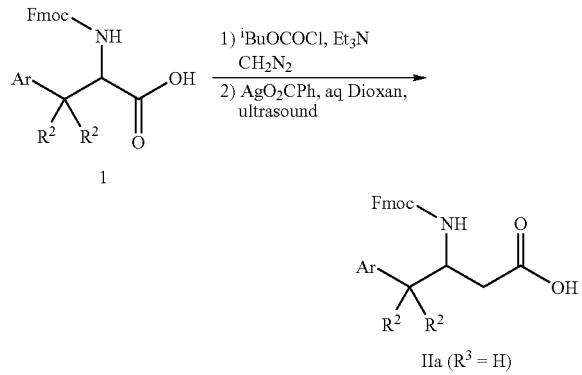

Compounds IIb, where $R^3$ is alkyl, may be conveniently prepared as described in Podlech et al., *Liebigs Ann.*, 1217 (1995) and illustrated in Scheme 2. An amino acid such as IIa, from Scheme 1, can be esterified either by treatment with a mineral acid such as hydrochloric acid in an alcoholic solvent, for example methanol, at temperatures of 0 to 60° C. for 2 to 48 hours, or by using a coupling agent such as dicyclohexylcarbodiimide and an alcohol such as methanol or benzyl alcohol in dichloromethane. The resultant ester can then be deprotonated with a hindered base such as lithium diisopropylamide at a temperature of −80 to −60° C. and alkylated by addition of an alkyl halide such as methyl or ethyl iodide. Removal of the ester can then be achieved by treatment with a base such as aqueous lithium hydroxide in a solvent such as THF, methanol or mixture of similar solvents. In the case of a benzyl ester, removal is achieved by catalytic hydrogenation using a palladium catalyst in a solvent such as methanol, ethyl acetate or mixture of such solvents.

SCHEME 2

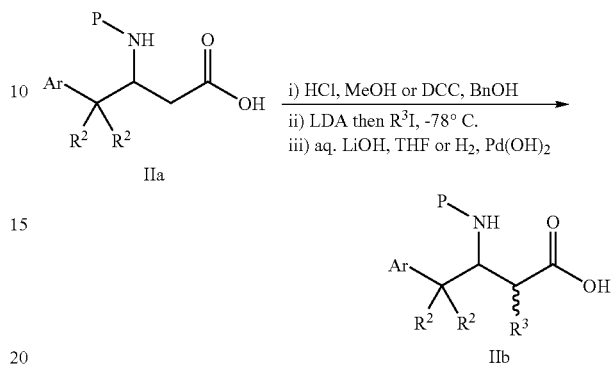

Compounds III are commercially available, known in the literature or may be conveniently prepared by a variety of methods familiar to those skilled in the art. One common route to the intermediates used below when X=O is described in Shaw et al., *Synthetic Commun.*, 1777 (1997) and illustrated in Scheme 3. A glycinol derivative 2 is coupled with 2-chloroacetyl chloride in a solvent such as dichloromethane or THF in the presence of a base such as aqueous sodium hydroxide. Cyclization of 3 is then effected by deprotonation of the alcohol with sodium hydride in THF at ambient temperature, followed by reduction of the amide with a hydride reducing agent such as lithium aluminum hydride in a polar solvent such as THF at 0 to 50° C. for 2 to 24 hours, to give amine IIIa.

SCHEME 3

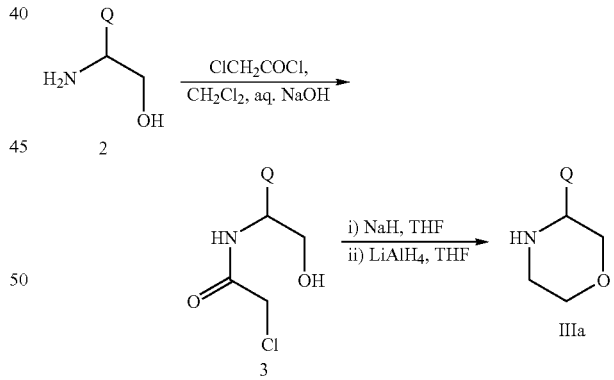

A convenient route for the preparation of amines III when X is $NR^7$ is illustrated in Scheme 4. A piperazine 4, which is suitably protected, for example as its tert-butyl or benzyl carbamate derivative, can be elaborated by alkylation of the piperazine nitrogen. This can be effected by treatment with an alkyl halide, in one example alpha-chloro-3-nitroacetanilide is used, in a polar solvent such as dimethylformamide (DMF), and a hindered base, for example diisopropylethylamine (DIEA), for 2 to 24 hours. The protecting group is then removed with, for example, trifluoroacetic acid in the case of Boc, or hydrobromic acid in acetic acid in the case of Cbz to give the desired amine IIIb.

SCHEME 4

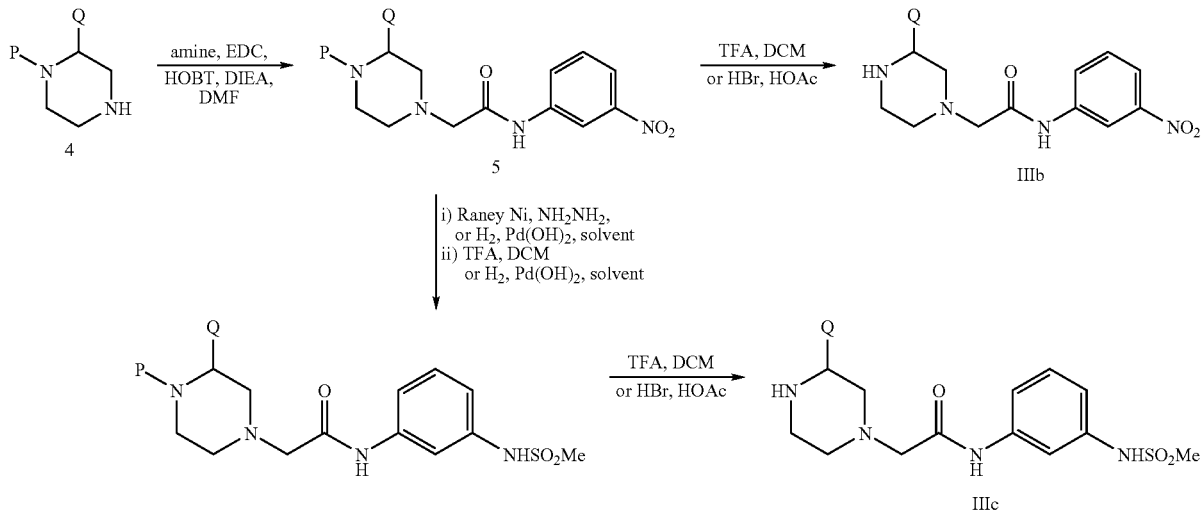

Compounds 4 from Scheme 4 are commercially available, known in the literature or may be conveniently prepared by a variety of methods familiar to those skilled in the art. In some cases, the coupling product 5 from the reactions described in Scheme 4 may be further modified, for example, by the manipulation of substituents on $R^7$. These manipulations may include, but are not limited to, reduction, oxidation, alkylation, acylation, and hydrolysis reactions which are commonly known to those skilled in the art. In one example, the nitro group in 5 is reduced using, for example Raney nickel and hydrazine in a polar solvent such as methanol at 25 to 60° C. for 0.5 to 3 hours to give an aniline which may be acylated using, for example, methanesulfonyl chloride, in a solvent such as methylene chloride and a base, generally pyridine or triethylamine, for 3 to 48 hours at ambient temperature. Deprotection as described above gives the desired amine IIIc.

An alternate route to compounds III, is described in Kiely et al., *Org. Preps. and Procedures Int.,* 22, 761, (1990) and illustrated in Scheme 5. An amino acid 6, which is suitably protected as, for example, its tert-butyl carbamate is coupled with an appropriate glycine derivative, such as N-benzylglycine ethyl ester, using a standard coupling reagent such as dicyclohexylcarbodiimide (DCC) or 1-ethyl-3-(3-dimethylaminopropyl)carbodiimide (EDC) in a solvent such as dichloromethane for 1 to 16 hours. The reaction may contain a catalyst such as N,N-dimethylamino-4-pyridine. The carbamate protecting group is then removed with, for example, hydrogen chloride in a solvent such as ethyl acetate at 0 to 25° C. for 3 to 24 hours, followed by an aqueous work up of the reaction using an inorganic base such as sodium bicarbonate to facilitate cyclization affording the diketopiperazine 7. Reduction to the piperazine IIId can be effected with a hydride reducing agent such as lithium aluminum hydride or borane-THF complex in a polar aprotic solvent generally tetrahydrofuran at 0 to 50° C. for 2 to 24 hours. In some cases, the reduction product IIId from the reactions described in Scheme 5 may be further modified, for example, by the manipulation of substituents on Q. These manipulations may include, but are not limited to, reduction, oxidation, alkylation, acylation, and hydrolysis reactions which are commonly known to those skilled in the art.

SCHEME 5

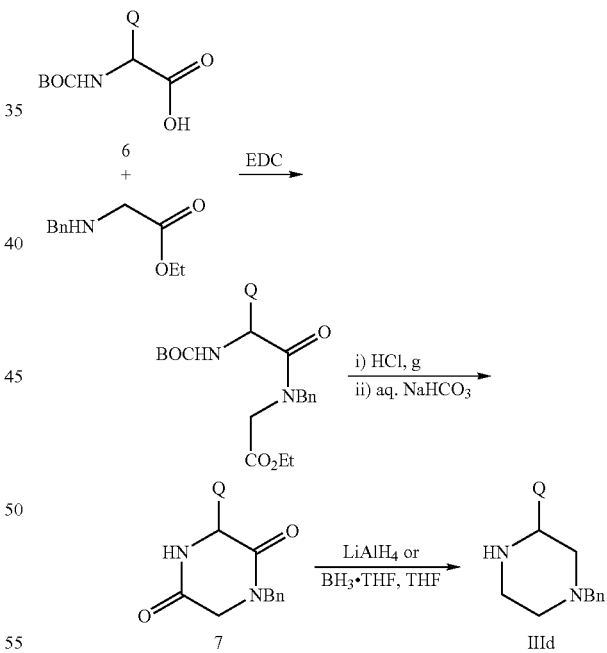

Intermediates II and III are coupled under standard peptide coupling conditions, for example, using 1-ethyl-3-(3-dimethylaminopropyl)carbodiimide (EDC), 1-hydroxybenzotriazole (HOBt), and a base, generally diisopropylethylamine, in a solvent such as N,N-dimethylformamide (DMF) or methylene chloride for 3 to 48 hours at ambient temperature to provide intermediate 8 as shown in Scheme 6. The protecting group is then removed with, for example, trifluoroacetic acid in the case of Boc to give compound I. The product is purified from unwanted side products by recrystallization, trituration, preparative thin layer chromatography, flash chromatography on silica gel as described by W. C. Still et al, *J. Org. Chem.*, 43, 2923 (1978), or HPLC. Compounds which are purified by HPLC may be isolated as the corresponding salt. Purification of intermediates is achieved in the same manner.

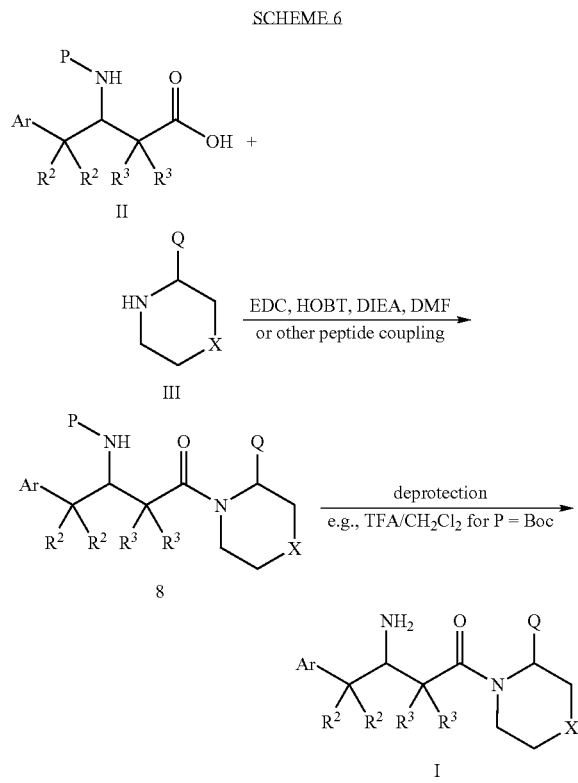

In some cases the intermediate 8 from the coupling reaction described in Scheme 6 may be further modified before removal of the protecting group, for example, by manipulation of substituents on $R^2$, $R^3$, Q or $R^7$ (when $X=NR^7$). These manipulations may include, but are not limited to, reduction, oxidation, alkylation, acylation, and hydrolysis reactions which are commonly known to those skilled in the art. One such example is illustrated in Scheme 7. Compound 8 ($X=NR^7=NBn$), which is prepared as outlined in Scheme 6 from Intermediate IIId, is reduced by catalytic hydrogenation using a palladium catalyst in a solvent such as methanol, ethyl acetate or a mixture of solvents to give amine 9. Alkylation of this amine with a group $R^7$ can be achieved as described in Scheme 4 or as shown in Scheme 7, by reaction with an aldehyde, for example paraformaldehyde, in a chlorinated solvent such as 1,2-dichloroethane with a reducing agent, generally sodium triacetoxyborohydride in the presence of a dehydrating agent such as 4A molecular sieves at ambient temperature for 1 to 24 hours. Protecting group removal is then achieved as described above to give amine Ic. Alternatively amine 9 can be arylated using chemistry known to those skilled in the art and described in Wolfe et. al., *J. Org. Chem.*, 65, 1158 (2000). In addition, amine 9 may be deprotected directly, as described above, to provide Ia ($R^7=H$).

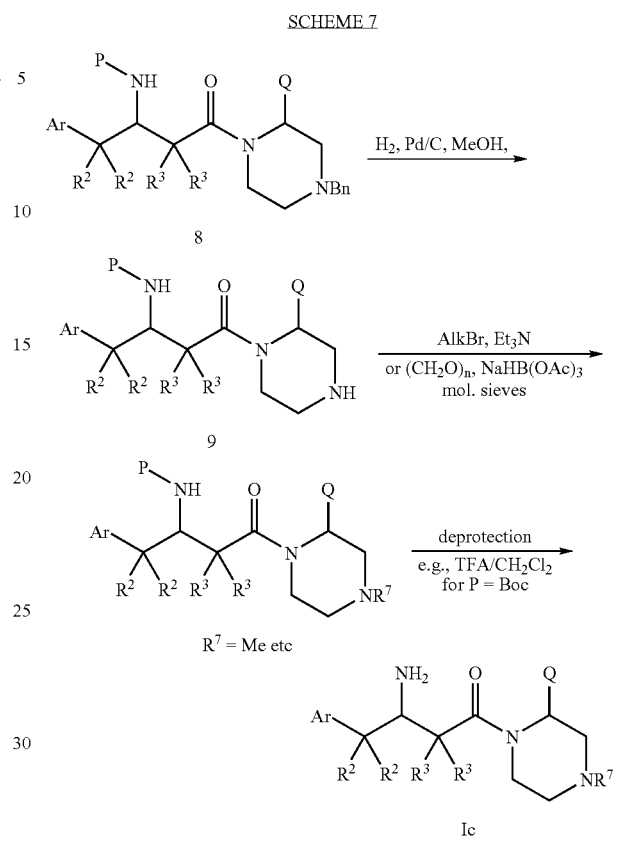

Another such example is illustrated in Scheme 8. Compound 8 is prepared as described in Scheme 6 using a beta amino acid II where $R^3=OP^1$ ($P^1$ being a suitable protecting group such as tert-butyldimethylsilyl). Such amino acids are commercially available, known in the literature or may be conveniently prepared by a variety of methods familiar to those skilled in the art. Compound 8 is then treated with a fluoride source such as tetrabutylammonium fluoride in a solvent, normally THF, for 2 to 48 hours to release the alcohol 10. This is then subsequently reacted with a fluorinating agent such as [bis(2-methoxyethyl)amino]sulfur trifluoride followed by removal of the protecting group as previously described to give the fluoro analog Id.

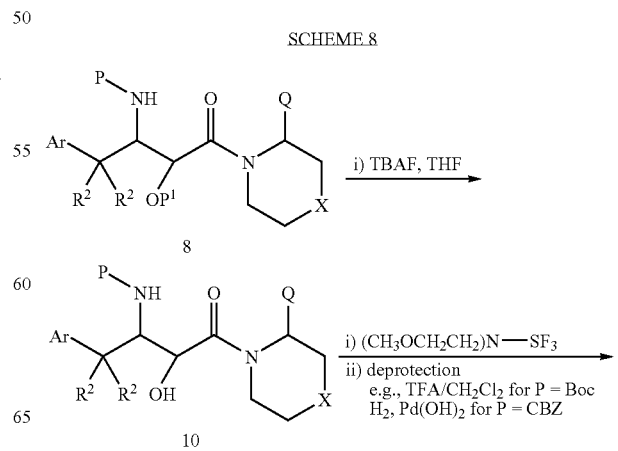

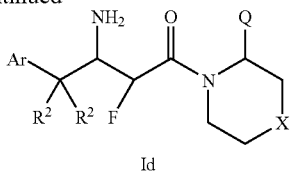

Id

EXAMPLES

The following examples are provided so that the invention might be more fully understood. These examples are illustrative only and should not be construed as limiting the invention in any way.

Example 1

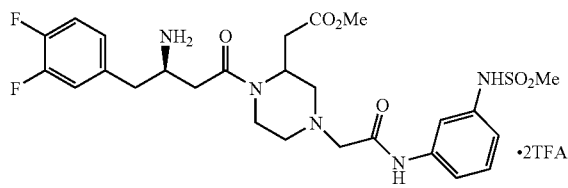

Step A. Methyl (4-{2-[(3-nitrophenyl)amino]-2-oxoethyl}piperazin-2-yl)acetate. To a solution of 1.5 g (5.83 mmol) of methyl (RS)-tert-butyl 2-(2-methoxy-2-oxoethyl)piperazine-1-carboxylate and 2.5 g (11.66 mmol) of alpha-chloro-3-nitroacetanilide in 50 mL of DMF was added 4.06 mL (23.32 mmol) of diisopropylethylamine (DIEA), and stirring was continued at ambient temperature for 16 h. The reaction was diluted with ethyl acetate and washed sequentially with water and brine, and dried over magnesium sulfate to give 7 g of a crude oil. Purification by flash chromatography (silica gel, 40 to 50% ethyl acetate in hexanes) yielded 3.9 g of protected piperazine. This was dissolved in 100 mL of a 1:1 mixture of methylene chloride:trifluoroacetic acid and the reaction was stirred for 2 h, before concentration in vacuo. The residual oil was dissolved in methylene chloride and concentrated to remove excess trifluoroacetic acid. Neutralization was effected by adding a solution of 10% concentrated ammonium hydroxide in methanol and concentration in vacuo, followed by dissolving the residue in ethyl acetate and washing sequentially with saturated sodium bicarbonate solution, water, and brine. The solution was dried over magnesium sulfate and concentrated in vacuo to yield 2.87 g of the title compound. $^1$H NMR (400 MHz, CD$_3$OD) δ 8.67 (s, 1H), 7.98–7.95 (m, 2H), 7.57 (t, 1H, J=8 Hz), 3.63 (s, 3H), 3.60–3.39 (m, 4H), 3.37–3.10 (m, 4H), 2.98–2.90 (m, 1H), 2.82–2.62 (m, 2H).

Step B. Methyl {1-[(3R)-3-amino-4-(3,4-difluorophenyl)butanoyl]-4-[2-({3-[(methyl-sulfonyl)amino]phenyl}amino)-2-oxoethyl]piperazin-2-yl}acetate, bistrifluoroacetate salt. To a solution of 0.298 g (0.889 mmol) of methyl (4-{2-[(3-nitrophenyl)amino]-2-oxoethyl}piperazin-2-yl)acetate in 5 mL of dimethylformamide (DMF) was added 0.336 g (1.07 mmol) of (3R)-3-[(tert-butoxycarbonyl)amino]-4-(2-fluorophenyl)butanoic acid, 0.205 g (1.07 mmol) of 1-ethyl-3-(3-dimethylaminopropyl)-carbodiimide hydrochloride (EDC), 180 mg (1.33 mmol) of 1-hydroxybenzotriazole hydrate (HOBT), and 0.386 mL (2.2 mmol) of diisopropylethylamine (DIEA). The mixture was stirred for 16 h and diluted with ethyl acetate. The organic phase was washed sequentially with water, saturated aqueous sodium bicarbonate solution, water, brine, dried over magnesium sulfate and the solvent removed in vacuo to yield crude product. This was immediately dissolved in 10 mL of methanol, palladium hydroxide on activated charcoal (~50 mg) was added, and the mixture was stirred under a balloon of hydrogen for 0.5 h. The reaction was diluted with methanol, filtered through a pad of Celite, and concentrated in vacuo. Purification using preparative thin layer chromatography (TLC) (silica gel, 4.5:0.5:95 methanol:concentrated ammonium hydroxide:methylene chloride) afforded 425 mg of the desired aniline. A portion (60 mg, 0.1 mmol), of this was dissolved in 3 mL of methylene chloride and 0.1 mL (1.2 mmol) of pyridine and 0.0116 mL (0.15 mmol) of methanesulfonyl chloride were added. The reaction was stirred for 16 h before concentration in vacuo and purification by preparative TLC (silica gel, 4.5:0.5:95 methanol:concentrated ammonium hydroxide:methylene chloride) to afford 54 mg of the title compound as its tert butyl carbamate.

A portion (15 mg) of this material was deprotected, as described in Step A above, to give the title compound which was isolated as its bistrifluoroacetate salt and not purified further. $^1$H NMR (400 MHz, CD$_3$OD) δ 7.63 (s, 1H), 7.38–7.21 (m, 4H), 7.13–7.07 (m, 1H), 6.99 (d, 1H, J=8 Hz), 3.95–3.50 (m, 11H), 3.30–3.18 (m, 1H), 3.10–2.95 (m, 3H), 2.98 (s, 3H), 2.90–2.79 (m, 2H), 2.75–2.60 (m, 2H).

Example 2

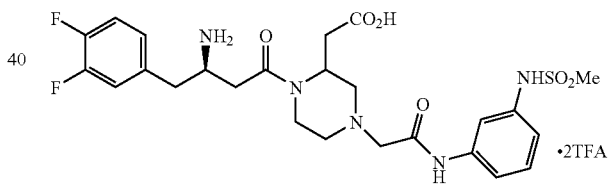

{1-[(3R)-3-Amino-4-(3,4-difluorophenyl)butanoyl]-4-[2-({3-[(methylsulfonyl)amino]-phenyl}-amino)-2-oxoethyl]piperazin-2-yl}acetic acid, bistrifluoroacetate salt. To a solution of 35 mg (0.051 mmol) of the tert-butyl carbamate of methyl {1-[(3R)-3-amino-4-(3,4-difluorophenyl)butanoyl]-4-[2-({3-[(methyl-sulfonyl)amino]phenyl}amino)-2-oxoethyl]piperazin-2-yl}acetate in 1.5 mL of THF was added 10 mg (0.255 mmol) of lithium hydroxide in 0.5 mL of water and the reaction was stirred for 16 h and concentrated in vacuo. The aqueous solution was acidified with 2N hydrochloric acid and extracted three times with ethyl acetate. The combined organic phase was washed with brine, dried over magnesium sulfate, and concentrated in vacuo to give 38 mg of product which was deprotected as described in Example 1, Step A, to give the title compound which was isolated as its bistrifluoroacetate salt and not purified further. $^1$H NMR (400 MHz, CD$_3$OD) δ 7.64 (s, 1H), 7.37–7.21 (m, 4H), 7.12–7.08 (m, 1H), 6.99 (d, 1H, J=8 Hz), 4.11–3.55 (m, 8H), 3.42–3.08 (m, 2H), 3.00–2.93 (m, 2H), 2.98 (s, 3H), 2.92–2.80 (m, 2H), 2.75–2.63 (m, 2H).

Example 3

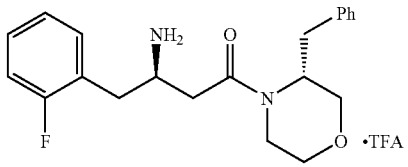

(2R)-4-[(3R)-3-Benzylmorpholin-4-yl]-1-(2-fluorophenyl)-4-oxobutan-2-amine, trifluoroacetate salt. To a solution of 16.5 mg (0.093 mmol) of (R)-3-(phenylmethyl)morpholine (prepared as described in Shawe et al; *Synthetic Communications,* 1777–1782, 1997) in 1 mL of dimethylformamide (DMF) was added 33 mg (0.11 mmol) of (3R)-3-[(tert-butoxycarbonyl)amino]-4-(2-fluorophenyl)butanoic acid, 21.3 mg (0.11 mmol) of 1-ethyl-3-(3-dimethylaminopropyl) carbodiimide hydrochloride (EDC), 18.9 mg (0.14 mmol) of 1-hydroxybenzotriazole hydrate (HOBT), and 0.041 mL (0.23 mmol) of diisopropylethylamine (DIEA). The mixture was stirred for 16 h and diluted with ethyl acetate. The organic phase was washed sequentially with water, saturated aqueous sodium bicarbonate solution, water, and brine, and dried over magnesium sulfate. The solvent was removed in vacuo and the compound purified by preparative TLC (silica gel, 50% ethyl acetate in hexanes) to give the product which was deprotected as described in Example 1, Step A, to give the title compound and isolated as its trifluoroacetate salt without further purification. $^1$H NMR (400 MHz, CD$_3$OD) δ 7.39–7.12 (m, 9H), 4.62–4.58 (m, 0.5H), 4.28 (d, 0.5H, J=15 Hz), 3.99–3.90 (m, 1H), 3.78–3.59 (m, 2.51), 3.51–3.39 (m, 3H), 3.27–3.19 (m, 0.5H), 3.05–2.49 (m, 5.5H), 1.8 (dd, 0.5H, J=8, 20 Hz).

Example 4

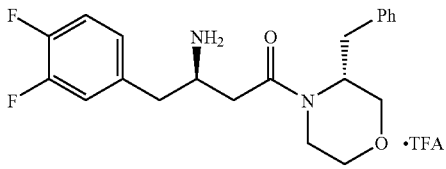

(2R)-4-[(3R)-3-Benzylmorpholin-4-yl]-1-(3,4-difluorophenyl)-4-oxobutan-2-amine, trifluoroacetate salt. In a manner identical to that described for Example 3, the title compound was prepared. $^1$H NMR (400 MHz, CD$_3$OD) δ 7.33–7.12 (m, 7H), 7.05–6.99 (m, 1H), 4.62–4.60 (m, 0.5H), 4.28 (d, 0.5H, J=15 Hz), 3.99–3.90 (m, 1H), 3.83–3.72 (m, 1.5H), 3.69–3.58 (m, 1H), 3.56–3.40 (m, 3H), 3.27–3.19 (m, 0.5H), 3.13–2.99 (m, 1.5H), 2.92–2.78 (m, 2H), 2.77–2.68 (1H), 2.65–2.60 (m, 0.5H), 2.53–2.48 (m, 1H), 1.78 (dd, 0.5H, J=8.20 Hz).

Example 5

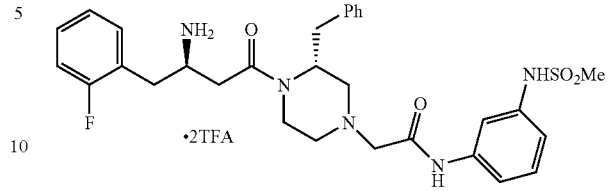

Step A. Benzyl 2-benzyl-4-{2-[(3-nitrophenyl)amino]-2-oxoethyl}piperazine-1-carboxylate. To a solution of 3.0 g (10.9 mmol) of (RS)-tert-butyl 2-benzylpiperazine-1-carboxylate in 30 mL of methylene chloride at 0° C. was added 2.3 mL (16.5 mmol) of triethylamine and 1.7 mL (11.9 mmol) of benzyl chloroformate. The resultant mixture was stirred at ambient temperature for 16 h and an additional 0.4 mL (2.8 mmol) of benzyl chloroformate was added. After stirring for a further 2 h, the reaction was partitioned between methylene chloride and water. The organic layer was washed sequentially with dilute hydrochloric acid, saturated sodium bicarbonate solution, and brine, dried over magnesium sulfate, and concentrated in vacuo to give 4-benzyl 1-tert-butyl 2-benzylpiperazine-1,4-dicarboxylate. The tert butyl carbamate was deprotected as described in Example 1, Step A to give 2.9 g of the free amine. A portion (1.5 g, 4.8 mmol), of this material was coupled with 1.6 g (7.5 mmol) of alpha-chloro-3-nitroacetanilide as described in Example 1, Step A, to give 1.3 g of the title compound as an off-white foamy solid. $^1$H NMR (400 MHz, CD$_3$OD) δ 8.70 (s, 1H), 7.99 (d, 1H, J=8 Hz), 7.96 (d, 1H, J=8 Hz), 5.58 (t, 1H, J=8 Hz), 7.36–7.05 (m, 10H), 5.00 (bs, 2H), 4.38–4.31 (m, 1H), 3.99 (d, 1H, J=16 Hz), 3.48 (td, 1H, J=16,2 Hz), 3.22–2.95 (m, 5H), 2.80 (d, 1H, J=14 Hz), 2.33–2.20 (m, 2H).

Step B. 2-(3-Benylpiperazin-1yl)-N-{3-[(methylsulfonyl) amino]phenyl}acetamide. To a solution of 1.3 g (2.66 mmol) of benzyl 2-benzyl-4-{2-[(3-nitrophenyl)amino]-2-oxoethyl}piperazine-1-carboxylate in 50 mL of a 1:1 mixture of methanol :1,2-dichloroethane was added 0.415 mL of hydrazine hydrate and 1.5 mL of a 50% suspension of Raney nickel in water. The reaction was stirred at 60° C. for 45 min, cooled, filtered through a Celite pad, washed with methanol, and concentrated in vacuo to yield 1.1 g of a foamy white solid which was used without further purification. A portion (0.51 g, 1.1 mmol), of this material was converted to the methanesulfonamide using the procedure described in Example 1, Step B, to yield 0.5 g of 2-(3-benzylpiperazin-1yl)-N-{3-[(methylsulfonyl)amino]phenyl}acetamide as its benzyl carbamate. The product was dissolved in 15 mL of methanol, palladium hydroxide on activated carbon (~200 mg) was added, and the mixture was stirred under a balloon of hydrogen for 24 h. The reaction was diluted with methanol, filtered through a pad of Celite, and concentrated in vacuo to afford 337 mg of 2-(3-benzylpiperazin-1yl)-N-{3-[(methylsulfonyl)-amino]phenyl}acetamide as a fluffy white solid which was used without further purification. $^1$H NMR (400 MHz, CD$_3$OD) δ 7.58 (s, 1H), 7.30–7.18 (m, 7H), 7.00–6.98 (m, 1H), 3.15–3.05 (m, 3H), 3.02–2.59 (m, 7H), 2.77–2.62 (m, 2H), 2.32–2.25 (m, 1H), 2.02 (t, 1H, J=14 Hz).

Step C. 2-{(3R)-4-[(3R)-3-Amino-4-(2-fluorophenyl)butanoyl]-3-benzylpiperazin-1-yl}-N-{3-[(methylsulfonyl) amino]phenyl}acetamide, bistrifluoroacetate salt. To a solution of 30 mg (0.075 mmol) of 2-(3-benzylpiperazin-1yl)-N-{3-[(methylsulfonyl)-amino]phenyl}acetamide in 3 mL of dimethylformamide (DMF) was added 25 mg (0.084 mmol) of (3R)-3-[(tert-butoxycarbonyl)amino]-4-(2-fluorophenyl)butanoic acid, 16 mg (0.083 mmol) of 1-ethyl-3-(3-dimethylaminopropyl)-carbodiimide hydrochloride (EDC), 14 mg (0.104 mmol) of 1-hydroxybenzotriazole hydrate (HOBT), and 0.030 mL (0.172 mmol) of diisopropylethylamine (DIEA). The mixture was stirred for 16 h and diluted with ethyl acetate. The organic phase was washed with water, saturated aqueous sodium bicarbonate solution, water, brine, dried over magnesium sulfate. The solvent was removed in vacuo and the product purified twice by preparative TLC (silica gel, 5% methanol in methylene chloride) to give the title compound as its tert-butyl carbamate. The product was deprotected as described in Example 1, Step A to give 32.9 mg of the product as a 1:1 mixture of diastereomers. Separation of the isomers was effected using reverse phase preparative HPLC (27% acetonitrile in water containing 0.1% trifluoroacetic acid) to give 8.3 mg of the title compound. $^1$H NMR (400 MHz, CD$_3$OD) δ 7.70 (s, 1H), 7.40–7.10 (m, 11H), 6.98 (d, 1H, J=7.4 Hz), 4.97–4.90 (m, 0.5H), 4.63 (d, 0.5H, J=15 Hz), 4.16–4.08 (m, 0.5H), 3.87–3.79 (m, 1.5H), 3.77–3.56 (m, 3H), 3.40–3.10 (m, 3H), 3.09–2.58 (m, 9.5H), 1.83 (dd, 0.5H, J=8.4, 16 Hz). Continued elution provided 9.6 mg of 2-{(3S)-4-[(3R)-3-amino-4-(2-fluorophenyl)-butanoyl]-3-benzylpiperazin-1-yl}-N-{3-[(methylsulfonyl)amino]phenyl}acetamide, bistrifluoroacetate salt. $^1$H NMR (400 MHz, CD$_3$OD) δ 7.71 (s, 1H), 7.42–7.06 (m, 11H), 6.98 (d, 1H, J=7.8 Hz), 4.98–4.90 (m, 0.5H), 4.63 (d, 0.5H, J=15 Hz), 4.20–4.13 (m, 0.5H), 3.82–3.79 (m, 1.5H), 3.75–3.58 (m, 1.5H), 3.42–3.10 (m, 4.5H), 3.09–2.40 (m, 9.5H), 1.75 (dd, 0.5H, J=2.16 Hz).

Example 6

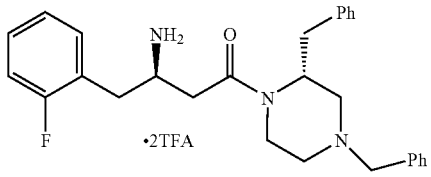

Step A. (R)-1,3-Dibenzylpiperazine. To a solution of 1.0 g (3.8 mmol) of N—BOC-D-phenyl alanine and 0.875 g (4.53 mmol) of N-benzylglycine ethyl ester in 15 mL of methylene chloride was added 0.863 g (4.5 mmol) of 1-ethyl-3-(3-dimethylaminopropyl)-carbodiimide hydrochloride (EDC) and a catalytic amount of N,N-dimethyl-4-aminopyridine. The reaction was stirred at ambient temperature for 16 h, concentrated in vacuo. The residue was suspended in ethyl acetate, and washed sequentially with dilute hydrochloric acid, saturated sodium bicarbonate solution, water, and brine, dried over magnesium sulfate, and concentrated in vacuo to give 1.21 g of coupled material as a white solid. This amide was suspended in 20 mL of ethyl acetate and cooled to 0° C. Hydrogen chloride was bubbled into the solution for 5 min and the reaction was stirred at ambient temperature for 2 h before concentration in vacuo. The residue was partitioned between methylene chloride and saturated sodium bicarbonate solution. The organic phase was washed sequentially with saturated sodium bicarbonate solution, and brine, dried over magnesium sulfate, and concentrated in vacuo to give 0.78 g of cyclic material. This material was added portionwise to a suspension of 0.485 g of lithium aluminum hydride in 20 mL of tetrahydrofuran at 0° C., and the reaction mixture was heated under reflux for 16 h. After cooling, 0.485 mL of water, 0.485 mL of 2N aqueous sodium hydroxide solution, and 1.5 mL of water were sequentially added in a dropwise manner. The white precipitate was removed by filtration through a Celite pad, and the filtrate was concentrated in vacuo. The crude material was suspended in ethyl acetate and washed with brine, dried over magnesium sulfate and reconcentrated to give 718 mg of (R)-1,3-dibenzylpiperazine which was used without further purification. $^1$H NMR (400 MHz, CDCl$_3$) δ 7.40–7.19 (m, 10H), 3.60–3.45 (m 2H), 3.20–3.15 (m, 1H), 3.09–3.05 (m, 1H), 3.00–2.75 (m, 5H), 2.33–2.26 (m, 1H), 2.17–2.10 (m, 1H).

Step B. (2R)-4-[(2R)-2,4-Dibenzylpiperazin-1-yl]-1-(2-fluorophenyl)-4-oxobutan-2-amine, bistrifluoracetate salt (R)-1,3-Dibenzylpiperazine (200 mg, 0.75 mmol) of was coupled to 357 mg (1.2 mmol) of (3R)-3-[(tert-butoxycarbonyl)amino]-4-(2-fluorophenyl)butanoic acid using the procedure outlined in Example 3 to give 471 mg of the final product as its tert-butyl carbamate.

A portion of the material was purified by preparative TLC (silica gel, 50% ethyl acetate in hexanes), and then deprotected as described in Example 1, Step A, to give the title compound which was isolated as its bistrifluoroacetate salt and not purified further. $^1$H NMR (400 MHz, CD$_3$OD) δ 7.58–7.43 (m, 5H), 7.40–7.00 (m, 9H), 5.02–4.95 (m, 0.5H), 4.80–4.72 (m, 0.5H), 4.59–4.46 (m, 1H), 4.30–4.19 (m, 1.5H), 4.01–3.95 (m, 0.5H), 3.77–3.60 (m, 2.5H), 3.40–2.58 (m, 9H), 1.82 (dd, 0.5H, J=8,17 Hz).

Example 7

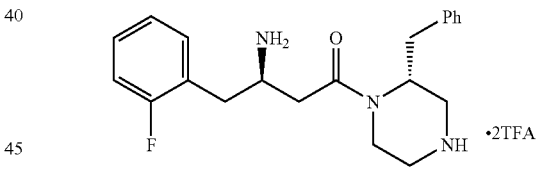

(2R)-4-[(2R)-2-Benzylpiperazin-1-yl]-1-(2-fluorophenyl)-4-oxobutan-2-amine, bis trifluoroacetate salt. To a solution of 502 mg (0.92 mmol) of the tert-butyl carbamate of (2R)-4-[(2R)-2,4-dibenzylpiperazin-1-yl]-1-(2-fluorophenyl)-4-oxobutan-2-amine in 20 mL of methanol, palladium hydroxide on activated carbon (~300 mg) was added, and the mixture was stirred under a balloon of hydrogen for 24 h. The reaction was diluted with methanol, filtered through a pad of Celite, and concentrated in vacuo to afford the desired product. A portion of the material was purified by preparative TLC (silica gel, 5% methanol in methylene chloride), and then deprotected as described in Example 1, Step A, to give the title compound which was isolated as its bistrifluoroacetate salt and not purified further. 1H NMR (400 MHz, CD$_3$OD) δ 7.40–7.00 (m, 9H), 5.15–5.05 (m, 0.5H), 4.77–4.68 (m, 0.5H), 4.32–4.25 (m, 0.5H), 3.95–3.85 (m, 0.5H), 3.75–3.56 (m, 1.5H), 3.43–3.20 (m, 3H), 3.19–2.82 (m, 5H), 2.80–2.65 (m, 1.5H), 2.58–2.50 (m, 0.5H), 1.68 (dd, 0.5H, J=8.17 Hz).

Example 8

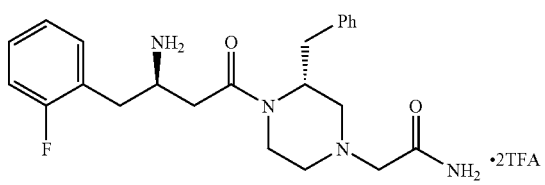

2-{(3R)-4-[(3R)-3-Amino-4-(2-fluorophenyl)butanoyl]-3-benzylpiperazin-1-yl}acetamide, bis trifluoroacetate salt. To a solution of 50 mg (0.11 mmol) of the tert-butyl carbamate of (2R)-4-[(2R)-2-benzylpiperazin-1-yl]-1-(2-fluorophenyl)-4-oxobutan-2-amine in 1 mL of N,N-dimethylformamide was added 31 mg (0.33 mmol) of 2-chloroacetamide and 0.1 mL (0.57 mmol) of diisopropylethylamine. The reaction mixture was stirred at ambient temperature for 16 h, diluted with ethyl acetate, washed with water and brine, dried over magnesium sulfate, and concentrated in vacuo. Purification by preparative TLC (silica gel, 5% methanol in methylene chloride) gave 24 mg of coupled product, which was deprotected as described in Example 1, Step A, to give 28 mg of the title compound which was isolated as its bistrifluoroacetate salt and not purified further. $^1$H NMR (400 MHz, CD$_3$OD) δ 7.40–7.10 (m, 9H), 5.02–4.93 (m, 0.5H), 4.75–4.66 (m, 0.5H), 4.23–4.17 (m, 0.5H), 3.97–3.80 (m, 1.5H), 3.76–3.60 (m, 2.5H), 3.55–3.30 (m, 2.5H), 3.19–2.65 (m, 7H), 2.60–2.53(m, 0.5H), 1.82 (dd, 0.5H, J=8.17 Hz).

Example 9

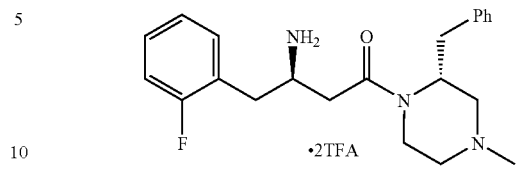

(2R)-4-[(2R)-2-Benzyl-4-methylpiperazin-1-yl]-1-(2-fluorophenyl)-4-oxobutan-2-amine, bistrifluoroacetate salt. To a solution of 88 mg (0.20 mmol) of the tert-butyl carbamate of (2R)-4-[(2R)-2-benzylpiperazin-1-yl]-1-(2-fluorophenyl)-4-oxobutan-2-amine in 2.5 mL of 1,2-dichloroethane was added 100 mg (0.47 mmol) of sodium triacetoxyborohydride, 100 mg of paraformaldehyde, and 4A molecular sieves. The reaction mixture was stirred at ambient temperature for 16 h, diluted with ethyl acetate, washed sequentially with saturated sodium bicarbonate solution, water and brine, dried over magnesium sulfate, and concentrated in vacuo. Purification by preparative TLC (silica gel, 5% methanol in methylene chloride) gave 77 mg of coupled product, which was deprotected as described in Example 1, Step A above, to give 80 mg of the title compound which was isolated as its bistrifluoroacetate salt and not purified further. $^1$H NMR (400 MHz, CD$_3$OD) δ 7.40–7.08 (m, 9H), 5.20–4.08 (m, 0.5H), 4.80–4.75 (m, 0.5H), 4.38–4.30 (m, 0.5H), 3.98–3.91 (m, 0.5H), 3.72–3.40 (m, 3.5H), 3.40–2.80 (m, 9H), 2.79–2.63 (m, 1.5H), 2.58–2.47(m, 0.5H), 1.65 (dd, 0.5H, J=8.17 Hz).

Following the procedures outlined for Examples 1–9, the compounds listed in Tables 1–3 were prepared as their bistrifluoroacetate salts (unless otherwise noted).

TABLE 1

| Example | Ar | Q | R$^7$ | Selected $^1$H NMR data of trifluoroacetate salts. |
|---|---|---|---|---|
| 10 | 3,4-diF—Ph | Bn | –CH$_2$C(O)NH-(3-NHSO$_2$Me-phenyl) | 7.71(s, 1H), 7.40–6.93 (m, 11H), 2.97(s, 3H) |
| 11 | 3,4-diF—Ph | H | H | 7.30–7.21(m, 2H), 7.12–7 08(m, 1H) |
| 12 | 3,4-diF—Ph | H | –CH$_2$C(O)NH-(3-NHSO$_2$Me-phenyl) | 7.68(t, 1H, J=1.8Hz), 7.36–7.22(m, 5H), 7.12–7.08(m, 1H), 6.98 (d, 1H, J=7.8Hz)4.14 (s, 2H), 2.97(s, 3H) |
| 13 | 3,4-diF—Ph | Bn | –CH$_2$C(O)NH-(3-NHSO$_2$CH$_2$CF$_3$-phenyl) | 7.73(s, 1H), 7.41–6.94 (m, 11H), 4.17–4.05(m, 2H) |

TABLE 1-continued

| Example | Ar | Q | R⁷ | Selected ¹H NMR data of trifluoroacetate salts. |
|---|---|---|---|---|
| 14 | 3,4-diF—Ph | Bn | 2-(1H-indol-3-yl)ethyl | 7.62–7.58(m 1H), 7.39–6.91(m, 12H) |
| 15 | 3,4-diF—Ph | Ph | CH₂C(O)NH-(3-NHSO₂Me-phenyl) | 7.61(s, 1H), 7.55–7.35 (m, 5H), 7.34–7.05(m, 5H), 6.99(d, 1H, J=8Hz), 2.97(s, 3H) |
| 16 | 3,4-diF—Ph | CH₂(3-indole) | CH₂C(O)NH-(3-NHSO₂Me-phenyl) | 7.83–7.73(m, 2H), 7.60–7.53(m, 1H), 7.41–6.73(m, 9H), 4.17–3.99(m, 2H) |
| 17 | 3,4-diF—Ph | 4-BrBn | Bn | 7.58–7.45(m, 5H), 7.41–7.10(m, 4H), 7.09–6.95(m, 3H) |
| 18 | 2-F—Ph | H | H | 7.39–7.30(m, 2H), 7.21–7.10(m, 2H) |
| 19 | 2-F—Ph | H | CH₂C(O)NH-(3-NHSO₂Me-phenyl) | 7.67(t, 1H, J=2Hz), 7.39–7.26(m, 4H), 7.22–7.13(m, 2H), 6.97 (d, 1H, J=7.8Hz), 4.09 (s, 2H), 2.97(s, 3H) |
| 20 | 2-F—Ph | H | CH₂(2-pyridyl) | 8.69(d, 1H, =4.5Hz), 7.98(td, 1H, J= 7.7, 1.6Hz), 7.58–7.50 (m, 2H), 7.38–7.31(m, 2H), 7.21–7.12(m, 2H), 4.47(s, 2H) |
| 21 | 2-F—Ph | H | CH₂(3-pyridyl) | 8.78(d, 1H, J=1.8Hz), 8.74(dd, 1H, J= 1.3, 5.3Hz), 8.27(d, 1H, J=8Hz), 7.78(dd, 1H, J=5.3, 8Hz), 7.39–7.31 (m, 2H), 7.21–7.12(m, 2H), 4.28(s, 2H) |
| 22 | 2-F—Ph | H | 2-(1H-indol-3-yl)ethyl | 7.70(d, 1H, J=7.9Hz), 7.54(s, 1H), 7.45(d, 1H, J=8.0Hz), 7.34–6.99(m, 6H), 4.58(s, 2H) |
| 23 | 2-F—Ph | H | adamantyl | 2.27(s, 3H), 2.00(s, 6H), 1.83–1.70(m, 6H) |

TABLE 1-continued
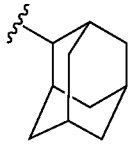
| Example | Ar | Q | R[7] | Selected $^1$H NMR data of trifluoroacetate salts. |
|---|---|---|---|---|
| 24 | 2-F—Ph | H | 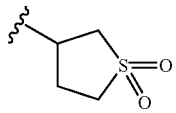 | 3.36(s, 1H), 2.43 (s, 2H), 2.08–1.89(m, 6H), 1.88–1.73(m, 6H) |
| 25 | 2-F—Ph | H | 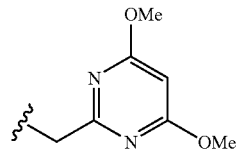 | 3.99–3.61(m, 6H), 3.57 (dd, 1H, J=12.5, 8.2Hz), 3.42–3.30(m, 2H), 3.26–2.98(m, 8H), 2.40–2.27(m, 1H) |
| 26 | 2-F—Ph | H | 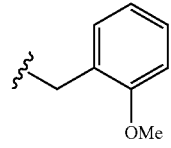 | Free base: 6.15(s, 1H), 4.49(s, 2H), 3.97(s, 6H) |
| 27 | 2-F—Ph | H | 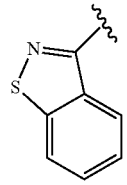 | 7.53–4.47(m, 1H), 7.42 (dd, 1H, 1.6, 7.7Hz), 7.20–7.11(m, 3H), 7.06 (t, 1H, J=7.5Hz), 4.38 (s, 2H), 3.92(s, 3H) |
| 28 | 2-F—Ph | H | 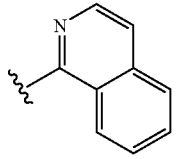 | 8.02(d, 1H, J=8.2Hz), 7.91(d, 1H, J= 8.2Hz), 7.56–7.52(m, 1H), 7.46–7.42(m, 1H) |
| 29 | 2-F—Ph | H | 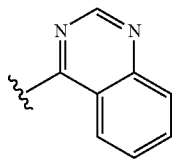 | 8.36(d, 1H, J=8.4Hz), 8.06–7.98(m, 2H), 7.85–7.81(m, 2H), 7.59 (d, 1H, J=6.8Hz) |
| 30 | 2-F—Ph | H | 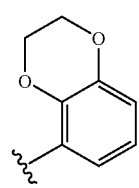 | 8.73(s, 1H), 8.28(d, 1H, J=8.4Hz), 8.05(t, 1H, J=8.0Hz), 7.82(d,1H, J = 8.4Hz), 7.79 –7.75(m, 1H) |
| 31 | 2-F—Ph | H |  | 6.78(t, 1H, J=8.0Hz), 6.63(dd, 1H, J= 1.3, 8.2Hz), 6.59(dd, 1H, J=1.3, 8.0Hz), 4.32–4.20(m, 4H) |

TABLE 1-continued
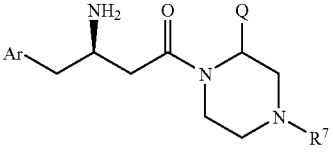
| Example | Ar | Q | R⁷ | Selected ¹H NMR data of trifluoroacetate salts. |
|---|---|---|---|---|
| 32 | 2-F—Ph | H | 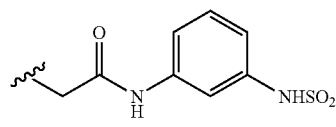 | 7.38–7.12(m, 8H), 4.13 (quin, 1H, J=7.8Hz), 3.44–3.20(m, 12H) |
| 33 | 2-F—Ph | Bn | 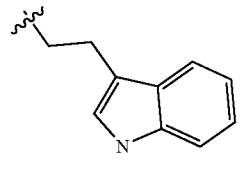 | 7.75(s, 1H), 7.41–7.08 (m, 11H), 7.01(d, 1H, J=7.8Hz), 4.16–4.05 (m, 2H) |
| 34 | 2-F—Ph | Bn | 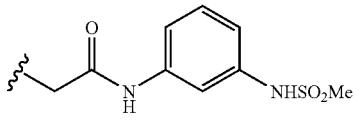 | 7.62–7.55(m, 1H), 7.41–7.00(m, 13H) |
| 35 | 2-F—Ph | Bn | Ph | 7.41–7.07(m, 11H), 6.99–6.82(m, 3H) |
| 36 | 2-F—Ph | Bn | 2-MeOPh | 7.42–6.86(m, 13H), 3.88(s, 1.2H), 3.87(s, 0.75, 3.86s, 1.05H) |
| 37 | 2-F—Ph | $CH_2CO_2Me$ | 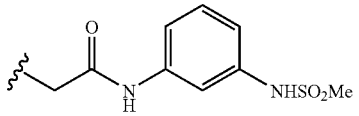 | 7.65(s, 1H), 7.39–7.25 (m, 4H0, 7.21–7.11(m, 2H), 6.97(d, 1H, J= 8Hz), 2.96(s, 3H) |
| 38 | 2-F—Ph | $CH_2CO_2H$ | 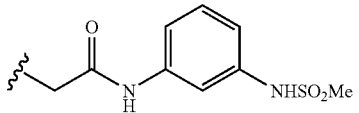 | 7.65(s, 1H), 7.38–7.25 (m, 4H), 7.21–7.11(m, 2H), 6.97(d, 1H, J= 8Hz), 2.97(s, 3H) |
| 39 | 2-F—Ph | Ph | 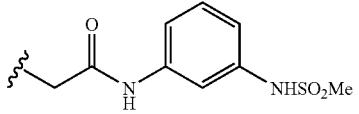 | 7.63(s, 1H), 7.55–7.10 (m, 11H), 6.99(d, 1H, J=8Hz), 2.97(s, 3H) |
| 40 | 2-F—Ph | $CH_2$(3-indole) | 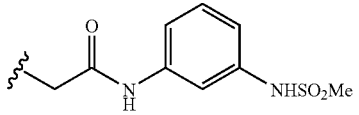 | 7.83–7.70(m, 2H), 7.60–7.45(m, 1H), 7.40–7.25(m, 4H), 7.23–7.05(m, 4H), 7.01–6.95(m, 2H), 4.17–3.99(m, 2H) |
| 41 | 2-F—Ph | 4-BrBn | Bn | 7.55–7.43(m, 5H), 7.1–7.10(m, 6H), 7.05(d, 0.5H, J=8Hz), 6.97(d, 1H, J=8Hz), 6.92(d, 0.5H, J=8Hz), |
| 42 | Ph | Bn |  | 7.72(s, 1H), 7.41–7.10 (m, 12H), 6.99(d, 1H, J=8Hz), 2.98(s, 3H) |

TABLE 1-continued

| Example | Ar | Q | R⁷ | Selected ¹H NMR data of trifluoroacetate salts. |
|---------|-----|-----|-----|---------|
| 43 | 4-ClPh | Bn | (acetamide linker to 3-NHSO₂Me phenyl) | 7.70(s, 1H), 7.41–7.08 (m, 11H), 6.99(d, 1H, J=8Hz), 2.98(s, 3H) |

TABLE 2

| Example | Ar | Q | R⁷ | Selected ¹H NMR data of trifluoroacetate salts |
|---------|-----|-----|-----|---------|
| 44 | 3,4-diF—Ph | Bn | Bn | 7.58–7.43(m, 5H), 7.31–6.98(m, 8H) |
| 45 | 3,4-diF—Ph | Bn | H | 7.38–7.07(m, 7H), 7.08–6.98(m, 1H) |
| 46 | 3,4-diF—Ph | 4-F—PhCH₂ | Bn | 7.56–7.45(m, 5H), 7.28–6.81(m, 7H) |
| 47 | 3,4-diF—Ph | 4-F—PhCH₂ | H | 7.29–7.21(m, 3H), 7.21–7.17(m, 1H), 7.12–6.93(m, 3H) |
| 48 | 3,4-diF—Ph | 3,4-F—PhCH₂ | Bn | 7.52–7.48(m, 5H), 7.30–6.93(m, 5H), 6.92–6.82(m, 1H) |
| 49 | 3,4-diF—Ph | 3,4-F—PhCH₂ | H | 7.30–7.15(m, 3H), 7.14–7.00(m, 3H) |
| 50 | 3,4-diF—Ph | 4-F—Ph | Bn | 7.57–7.47(m, 5H), 7.30–7.03(m, 7H) |
| 51 | 3,4-diF—Ph | 4-F—Ph | H | 7.46–7.03(m, 7H) |
| 52 | 2-F—Ph | ⁱPr | Bn | 1.80–1.65(m, 1H), 1.52–1.35(m, 2H), 0.92–0.83(m, 6H) |
| 53 | 2-F—Ph | ⁱPr | H | 1.80–1.62(m, 1H), 1.59–1.40(m, 2H), 0.96–0.86(m, 6H) |
| 54 | 2-F—Ph | Me | Bn | 1.39–1.20(m, 3H) |
| 55 | 2-F—Ph | Me | H | 1.40–1.23(m, 3H) |
| 56 | 2-F—Ph | 4-F—PhCH₂ | Bn | 7.56–7.43(m, 5H), 7.39–7.03(m, 6H), 7.00–6.79(m, 2H) |
| 57 | 2-F—Ph | 4-F—PhCH₂ | H | 7.39–7.35(m, 1H), 7.30–7.03(m, 6H), 6.95(t, 1H, J=10Hz) |
| 58 | 2-F—Ph | 3,4-F—PhCH₂ | Bn | 7.55–7.43(m, 5H), 7.39–7.22(m, 2H), 7.21–6.93(m, 4H), 6.90–6.81(m, 1H) |
| 59 | 2-F—Ph | 3,4-F—PhCH₂ | H | 7.39–6.98(m, 7H) |
| 60 | 2-F—Ph | 4-F—Ph | Bn | 7.57–7.47(m, 5H), 7.42–7.08(m, 8H) |
| 61 | 2-F—Ph | 4-F—Ph | H | 7.50–7.00(m, 8H) |
| 62 | 3-thiophene | Bn | H | 7.46(dd, 1H, J=3,5Hz), 7.38-7.10(m, 6H), 6.97(d, 1H, 4.7Hz) |

TABLE 3

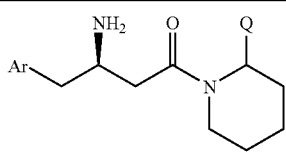

| Example | Ar | Q | Selected ¹H NMR data of trifluoroacetate salts |
|---|---|---|---|
| 63 | 3,4-diF—Ph | Bn | 7.31–6.92(m, 8H), 1.91–1.60(m, 4H), 1.58–1.30(m, 2H) |
| 64 | 2-F—Ph | Bn | 7.40–7.01(m, 9H) |
| 65 | 2-F—Ph | H | 7.39–7.31(m, 2H), 7.20–7.12(m, 2H), 1.70–1.61(m, 2H), 1.58–1.50(m, 4H) |
| 66 | 2-F—Ph | Me | 1.22–1.11(m, 3H) |

What is claimed is:

1. A compound of Formula I:

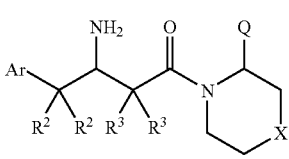

or a pharmaceutically acceptable salt thereof, wherein:
X is $NR^7$;
Ar is selected from the group consisting of:
  (1) phenyl and
  (2) naphthyl,
wherein Ar is optionally substituted with 1–5 groups $R^1$;
$R^1$ is selected from the group consisting of:
  (1) halogen,
  (2) $C_{1-6}$alkyl, which is linear or branched and is optionally substituted with 1–5 halogens,
  (3) $OC_{1-6}$alkyl, which is linear or branched and is optionally substituted with 1–5 halogens, and
  (4) CN;
Each $R^2$ is independently selected from the group consisting of H, OH, halogen and $C_{1-6}$alkyl, wherein $C_{1-6}$alkyl is linear or branched and is optionally substituted with 1–5 halogens, wherein the two groups $R^2$ can optionally be joined to form a $C_{3-6}$cycloalkyl, which is optionally substituted with 1–3 halogens;
Each $R^3$ is independently selected from the group consisting of H, halogen and $C_{1-6}$alkyl, wherein $C_{1-6}$alkyl is linear or branched and is optionally substituted with 1–5 halogens, wherein the two groups $R^3$ can optionally be joined to form a $C_{3-6}$cycloalkyl, which is optionally substituted with 1–3 halogens;
Q is selected from the group consisting of:
  (1) H,
  (2) $C_{1-10}$alkyl, which is linear or branched and is optionally substituted with 1–6 substituents independently selected from 0–5 halogens and 0–1 substituent selected from
    (a) phenyl,
    (b) naphthyl,
    (c) a 5 or 6-membered heterocycle which may be saturated or unsaturated comprising 1–4 heteroatoms independently selected from N, S and O,
    (d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5- or 6-membered heterocycle having 1–3 heteroatoms selected from N, S and O,
    (e) $CO_2H$,
    (f) $CO_2C_{1-6}$alkyl, and
    (g) $CONR^4R^4$
wherein said phenyl and naphthyl are optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens, and wherein said $CO_2C_{1-6}$alkyl is linear or branched, and wherein said 5 or 6-membered heterocycle and said 8–10 membered bicyclic ring system are optionally substituted with 1–5 substituents independently selected from $C_{1-6}$alkyl, $OC_{1-6}$alkyl, oxo, hydroxy and halogen, said $C_{1-6}$alkyl and $OC_{1-6}$alkyl being linear or branched and optionally substituted with 1–5 halogens, and wherein said $CO_2C_{1-6}$alkyl is linear or branched;
  (3) CN;
  (4) Phenyl, which is optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens;
  (5) Naphthyl, which is optionally substituted with 1–5 substituents independently selected from $C_{1-6}$alkyl, $OC_{1-6}$alkyl, hydroxy and halogen, said $C_{1-6}$alkyl and $OC_{1-6}$alkyl being linear or branched and optionally substituted with 1–5 halogens,
  (6) a 5 or 6-membered heterocycle which may be saturated or unsaturated comprising 1–4 heteroatoms independently selected from N, S and O, said heterocycle being optionally substituted with 1–5 substituents independently selected from oxo, hydroxy, $C_{1-6}$alkyl, $OC_{1-6}$alkyl and halogen, said $C_{1-6}$alkyl and $OC_{1-6}$alkyl being linear or branched and optionally substituted with 1–5 halogens, and
  (7) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O, wherein said bicyclic ring system is optionally substituted with 1–5 substituents independently selected from oxo, hydroxy, $C_{1-6}$alky, $OC_{1-6}$alkyl and halogen, said $C_{1-6}$alkyl and $OC_{1-6}$alkyl being linear or branched and optionally substituted with 1–5 halogens;
$R^4$ is selected from
  (1) H, and
  (2) $R^5$;
$R^5$ is selected from the group consisting of phenyl, $C_{3-6}$cycloalkyl and $C_{1-6}$alkyl, wherein $C_{1-6}$alkyl is linear or branched and is optionally substituted with 1–6 substituents independently selected from 0–5 halogens and 0–1 phenyl, wherein said optional phenyl substituent and said $R^5$ when R5 is phenyl or $C_{3-6}$cycloalkyl are optionally substituted with 1–5 substituents independently selected from halogen, OH, $C_{1-6}$alkyl, and $OC_{1-6}$alkyl, said $C_{1-6}$alkyl and $OC_{1-6}$alkyl being linear or branched and optionally substituted with 1–5 halogens; and
$R^7$ is selected from the group consisting of
  (1) H,
  (2) $C_{1-6}$alkyl which is linear or branched and is optionally substituted with 1–6 substituents independently selected from 0–5 halogens and 0–1 substituents selected from
    (a) phenyl,
    (b) naphthyl, (c) a 5 or 6-membered heterocyclic ring which may be saturated or unsaturated comprising 1–4 heteroatoms independently selected from N, S and O, (d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5- or 6-membered heterocycle having 1–3 heteroatoms selected from N, S and O, (e) C(=O)NR$^4$R$^4$, wherein said phenyl, naphthyl, and R$^4$ when R$^4$ is phenyl or C$_{3-6}$cycloalkyl are optionally substituted with 1–5 substituents independently selected from halogen, OH, nitro, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, and wherein said 5-6-membered heterocycle and 8–10 membered bicyclic ring system are optionally substituted with 1–5 substituents independently selected from halogen, oxo, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, (3) Phenyl, which is optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens, (4) a 5 or 6-membered heterocycle which may be saturated or unsaturated comprising 1–4 heteroatoms independently selected from N, S and O, wherein said heterocycle is optionally substituted with 1–5 substituents independently selected from halogen, oxo, OH, C$_{1-6}$alkyl and OC$_{1-6}$alkyl, said C$_{1-6}$alkyl and OC$_{1-6}$alkyl being linear or branched and optionally substituted with 1–5 halogens, (5) an 8–10 membered bicyclic ring system which may be saturated or unsaturated which comprises (a) two fused heterocyclic rings, each heterocyclic ring having 1–4 heteroatoms selected from N, S and O, or (b) a 5- or 6-membered heterocycle having 1–3 heteroatoms selected from N, S and O fused to a phenyl ring, wherein said bicyclic ring system is optionally substituted with 1–5 substituents independently selected from halogen, oxo, OH, C$_{1-6}$alkyl and OC$_{1-6}$alkyl, said C$_{1-6}$alkyl and OC$_{1-6}$alkyl being linear or branched and optionally substituted with 1–5 halogens, (6) adamantyl, which is optionally substituted with 1–5 substituents independently selected from halogen, OH, C$_{1-6}$alkyl and OC$_{1-6}$alkyl, said C$_{1-6}$alkYl and OC$_{1-6}$alkyl being linear or branched and optionally substituted with 1–5 halogens;

(7) naphthyl, which is optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens; and (8) a 5–6 membered cycloalkyl fused to a phenyl ring, wherein said cycloalkyl may be saturated or unsaturated, wherein said cycloalkyl and fused phenyl ring are optionally substituted with 1–5 substituents independently selected from halogen, OH, C$_{1-6}$alkyl and OC$_{1-6}$alkyl, said C$_{1-6}$alkyl and OC$_{1-6}$alkyl being linear or branched and optionally substituted with 1–5 halogens;

with the proviso that X is not N–Me.

2. A compound of formula I as recited in claim 1, wherein R$_2$ and R$_3$ are H.

3. A compound of formula I as recited in claim 1, wherein Ar is phenyl, optionally substituted as in claim 1.

4. A compound of formula I as recited in claim 1, wherein Q is selected from the group consisting of phenyl and CH$_2$phenyl, optionally substituted as in claim 1.

5. A compound of formula I as recited in claim 1, wherein X is NR$^7$, and R$^7$ is CH$_2$, which is substituted with 1 substituent selected from (a) phenyl;

(b) naphthyl;

(c) a 5 or 6-membered heterocyclic ring which may be saturated or unsaturated comprising 1–4 heteroatoms independently selected from N, S and O;

(d) an 8–10 membered bicyclic ring system which may be saturated or unsaturated which comprises (a) two fused heterocyclic rings, each heterocyclic ring having 1–4 heteroatoms independently selected from N, S and O, or (b) a phenyl ring fused to a 5-or 6-membered heterocycle having 1–3 heteroatoms selected from N, S and O, and (e) C(=O)NR$^4$R$^4$, wherein R$^4$ is as previously defined, and said phenyl, naphthyl, and R$^4$ when R$^4$ is phenyl or C$_{3-6}$cycloalkyl are optionally substituted with 1–5 substituents independently selected from halogen, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO$_2$C$_{1-6}$alkyl being linear or branched and optionally substituted with 1–5 halogens, and wherein said 5-6-membered heterocycle and 8–10 membered bicyclic ring system are optionally substituted with 1–5 substituents independently selected from halogen, oxo, OH, C$_{1-6}$alkyl, OC$_{1-6}$alkyl, and NHSO$_2$C$_{1-6}$alkyl, said C$_{1-6}$alkyl, OC$_{1-6}$alkyl and NHSO2C$_{1-6}$alkyl being linear or branched and optionally substituted with 1–5 halogens.

6. A compound of Formula I as recited in claim 1, wherein said 8–10 membered bicyclic ring system is selected from the group consisting of indole, indoline, benzofuran, benzothiophene, benzoxazole, benzisoxazole, benzothiazole, benzisothiazole, benzimidazole, benzimidazoline, quinoline, quinazoline, dihydroquinazoline, dihydroquinoline, isoquinoline, tetrahydroisoquinoline, and dihydroisoquinoline.

7. A compound of Formula I as recited in claim 1, wherein said 5-or 6-membered heterocycle is selected from the group consisting of furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, and tetrazolidine.

8. A compound of Formula Ia:

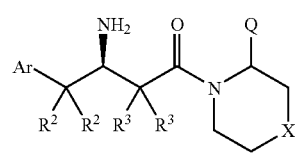

or a pharmaceutically acceptable salt thereof, wherein $R^1$, $R^2$, $R^3$, $R^4$, $R^5$, $R^7$, Q, X and Ar are as previously defined in claim 1; with the proviso that X is not N-Me.

9. A compound of Formula Ib:

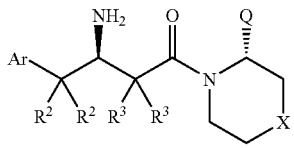

Ib or a pharmaceutically acceptable salt thereof, wherein $R^1$, $R^2$, $R^3$, $R^4$, $R^5$, $R^7$, Q, X and Ar are as previously defined in claim 1; with the proviso that X is not N-Me.

10. A pharmaceutical composition comprising a compound of claim 1 and a pharmaceutically acceptable carrier.

11. A method for treating non-insulin dependent (Type 2) diabetes mellitus in a mammalian patient in need of such treatment which comprises administering to said patient a therapeutically effective amount of a compound of claim 1.

* * * * *